United States Patent
Matsushima et al.

(10) Patent No.: US 6,719,989 B1
(45) Date of Patent: *Apr. 13, 2004

(54) SUSTAINED RELEASE DRUG CARRIER, AND METHOD OF MANUFACTURING SUSTAINED RELEASE DRUG CARRIER

(75) Inventors: Asako Matsushima, Saitama (JP); Masanori Nakasu, Tokyo (JP); Makoto Otsuka, Hyougo (JP)

(73) Assignee: PENTAX Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/658,021

(22) Filed: Sep. 8, 2000

(30) Foreign Application Priority Data

Sep. 8, 1999 (JP) ........................................ H11-254470

(51) Int. Cl.⁷ ..................... A61F 13/00; A61F 2/00; A61F 2/28; A61K 9/00; A61K 9/14
(52) U.S. Cl. .................. 424/422; 424/400; 424/423; 424/484; 623/16.11; 623/23.56; 623/23.57
(58) Field of Search ................... 424/422, 423, 424/426, 484, 400; 623/16.11, 23.56, 23.57, 23.6, 23.61; 156/89.11

(56) References Cited

U.S. PATENT DOCUMENTS

| | | | |
|---|---|---|---|
| 4,218,255 A | * | 8/1980 | Bajpai et al. ................. 106/45 |
| 4,293,540 A | * | 10/1981 | Shikita et al. ................ 424/26 |
| 4,878,914 A | * | 11/1989 | Miwa et al. .................. 623/16 |
| 5,030,611 A | | 7/1991 | Ogawa et al. |
| 5,055,307 A | | 10/1991 | Tsuru et al. |
| 5,645,596 A | * | 7/1997 | Kim et al. ................ 623/17.16 |
| 5,783,248 A | * | 7/1998 | Lin et al. ................... 427/2.27 |
| 5,851,670 A | | 12/1998 | Mitoh et al. |
| 5,897,953 A | | 4/1999 | Ogawa et al. |
| 5,919,473 A | | 7/1999 | Elkhoury ................... 424/422 |
| 6,040,196 A | | 3/2000 | Mitoh et al. |

FOREIGN PATENT DOCUMENTS

| | | |
|---|---|---|
| JP | 10279471 | 10/1998 |
| WO | 98/17330 | 4/1998 |
| WO | 98/38948 | 9/1998 |

OTHER PUBLICATIONS

M. Otsuka et al., "Controlled Drug Release from Hetero Porous Hydroxyappatite Block", with English Translation.

* cited by examiner

Primary Examiner—Thurman K. Page
Assistant Examiner—Humera N. Sheikh
(74) Attorney, Agent, or Firm—Greenblum & Bernstein, P.L.C.

(57) ABSTRACT

A sustained release drug carrier comprises a ceramic composite which is formed by bonding a plurality of ceramic bodies together, and drugs impregnated into the ceramic composite. A method of manufacturing the sustained release drug carrier comprises the steps of: (i) preparing ceramic bodies to be bonded together, each of the ceramic bodies having a bonding surface; (ii) preparing a slurry in which primary particles of a bonding ceramics are dispersed; (iii) applying the slurry to the bonding surface of at least one of the ceramic bodies to be bonded; (iv) sintering the ceramic bodies between which the slurry has been interposed to bond them together, to obtain a ceramic composite; and (v) impregnating a drug into the obtained ceramic composite. According to the structure and method described above, it is possible to provide a sustained release drug carrier whose drug release properties can be controlled and which is capable of exhibiting better drug release action suitable for the application sites, type of drugs to be carried, and the like.

18 Claims, 9 Drawing Sheets

FRONT ⟷ BACK

SUSTAINED RELEASE DRUG CARRIER, AND METHOD OF MANUFACTURING SUSTAINED RELEASE DRUG CARRIER

BACKGROUND OF THE INVENTION

1. Field of the Invention

The present invention relates to a sustained release drug carrier, and more particularly to a sustained release drug carrier suitable for medical use.

2. Description of the Prior Art

Hydroxyapatite, which is a calcium phosphate-based ceramic, has structure similar to inorganic components of the bone. For this reason, hydroxyapatite has excellent biocompatibility and is used for various biocompatible materials such as artificial dental implants, bone replacement materials, dental cements, and the like.

In clinical practice, hydroxyapatite is used by being formed into dense articles, granular articles, porous articles having arbitrary porosity, and the like.

As for examples of such clinical applications of the hydroxyapatite, sustained release drug carriers which are formed of calcium phosphate-based ceramic and which carry sustained release drug can be mentioned. These sustained release drug carriers are capable of continuously releasing the drug into the body over long periods of time.

Using such a sustained release drug carrier makes it possible to maintain an effective drug concentration in a localized area of the body. This results in fewer side effects in comparison with systemic drug administration such as oral administration and parenteral administration. Therefore, treatments using such sustained release drug carriers draw attention as one of the effective therapeutic methods.

However, the above-described conventional sustained release drug carriers involve the following drawbacks.

A dense sustained release drug carrier has sufficient strength for an implant material or the like, but it is not possible to carry a sufficient amount of drug and release them in an adequate manner.

On the other hand, a porous sustained release drug carrier can adequately carry and release a drug, but it rapidly releases a large amount of drug in the initial release stage. In other words, prolonged release of the drug at constant rates is difficult to achieve.

Another drawback of a porous sustained release drug carrier is that it is difficult to give this carrier sufficient strength necessary for an implant material.

SUMMARY OF THE INVENTION

Therefore, it is an object of the present invention to provide a sustained release drug carrier whose drug release properties can be controlled and which is capable of exhibiting better drug release action suitable for the application sites, type of drugs to be carried, and the like.

Another object of the present invention is to provide a method for manufacturing such a sustained release drug carrier.

In order to achieve the above objects, the present invention is directed to a sustained release drug carrier comprising:

a ceramic composite which is formed by bonding a plurality of ceramic bodies together; and drugs impregnated into the ceramic composite.

According to the present invention, it is possible to provide a sustained release drug carrier whose drug release properties can be controlled and which is capable of exhibiting better drug release action suitable for the application sites, type of drugs to be carried, and the like.

In this invention, it is preferred that the ceramic bodies have different porosities.

Further, in this invention, it is also preferred that at least one of the ceramic bodies has porosity of 5 to 90%.

Furthermore, in this invention, it is also preferred that the average pore size of at least one of the ceramic bodies lies within the range of 100 to 500 $\mu$m.

Moreover, in this invention, it is also preferred that the pores include three-dimensionally communicating pores having capillaries. In this case, the average pore size of the capillaries preferably lies within the range of 0.1 to 20 $\mu$m.

Still further, in this invention, it is also preferred that each of the ceramic bodies is formed from the same material.

Still further, in this invention, it is also preferred that at least one of the ceramic bodies is composed of a calcium phosphate-based compound. In this case, it is preferable that the calcium phosphate-based compound has a Ca/P ratio of 1.0 to 2.0. Preferably, the calcium phosphate-based compounds is hydroxyapatite.

Still further, in this invention, it is also preferred that the drugs include biologically active substances.

Still further, in this invention, it is also preferred that the ceramic composite is configured as a bone replacement material.

The present invention is also directed to a method of manufacturing a sustained release drug carrier, the method comprising the steps of:

preparing ceramic bodies to be bonded together, each of the ceramic bodies having a bonding surface;

preparing a slurry in which primary particles of a bonding ceramics are dispersed;

applying the slurry to the bonding surface of at least one of the ceramic bodies to be bonded;

sintering the ceramic bodies between which the slurry has been interposed to bond them together, to obtain a ceramic composite; and impregnating a drug into the obtained ceramic composite.

In this invention, it is preferred that the bonding ceramics in the slurry is constituted from the same material as that of at least one of the ceramic bodies to be bonded.

Further, in this invention, it is also preferred that the bonding ceramics is composed of a calcium phosphate-based compound. In this case, the calcium phosphate-based compounds preferably include hydroxyapatite.

These and other objects, structures and advantages of the present invention will be apparent more clearly from the following description of the invention based on the examples.

DETAILED DESCRIPTION OF THE PREFERRED EMBODIMENTS

Hereinafter, a sustained release drug carrier and a ceramic composite used for the sustained release drug carrier according to the present invention will be described in detail with reference to the accompanying drawings.

In this connection, the description is given with reference to the case where the sustained release drug carrier of the present invention is configured as a ceramic composite into which drugs is impregnated.

The features of the sustained release drug carrier according to the present invention is that drugs are carried by a ceramic composite obtained by bonding a plurality of ceramic bodies. The ceramic composite with the drugs constitutes the sustained release drug carrier of the present invention.

According to the sustained release drug carrier having such a feature, it is possible to control drug releasing rates appropriately. Further, it is also possible to provide a sustained release drug carrier having both strength and tissue affinity suitable for the application site.

In this connection, it is preferred that the ceramic composite is formed by bonding ceramics bodies having different porosities together. By bonding the ceramic bodies having different porosities together in this way, it is possible to obtain a sustained release drug carrier configured as a single unit and having desired drug retention capabilities, sustained drug releasabilities, physical properties, and the like. For example, according to the present invention, it is possible to obtain a sustained release drug carrier composed of a plurality of parts having different properties such as drug retention capabilities, sustained drug releasabilities, physical properties, respectively. Furthermore, according to the present invention, it is also possible to control the properties (function) of the sustained release drug carrier.

Specifically, for example, when a low-porosity ceramic body as a barrier layer is bonded around a high-porosity ceramic body (which can hold (or carry) a large amount of drug) to form the ceramic composite for the sustained release drug carrier, it becomes possible to reduce the drug releasing rate and to extend the drug release period.

Further, when a low-porosity ceramic body is bonded to a part of a high-porosity ceramic body to form the ceramic composite, it becomes possible to obtain a sustained release drug carrier in which sustained drug releasabilities of the respective ceramic bodies are different from each other. Specifically, configuring a sustained release drug carrier in this manner allows a drug to be released at a relatively high rate through the exposed portions of the high-porosity ceramic body. On the other hand, the drug is released at a relatively low rate from the exposed portions of the low-porosity ceramic body.

Furthermore, when the sustained release drug carrier is constructed so that each of the ceramic bodies thereof has a drug of different concentration, it becomes possible to release the drug having different concentrations successively.

In this case, it is preferred that the high porosity portions are arranged in sections of the ceramic composite which will be in contact with bones or tissues when implanted, which makes it possible to promote cohesion with bones and tissues. On the other hand, it is preferred that the low porosity portions are arranged in sections of the ceramic composite which serve to maintain the shape of the implanted space for the ceramic composite or serve to support the bones adjacent to the implanted space.

Various manufacturing methods can be used for manufacturing the ceramic bodies to be bonded together. For example, a dense ceramic body (ceramic body having a small porosity) may be manufactured in the following manner. Specifically, a starting material ceramic powder is first prepared in accordance with a wet or dry process. Subsequently, the starting material ceramic powder is pressurized by means of a mold press, rubber press or the like to form a compacted body having a predetermined shape. Thus formed compacted body is then sintered at a predetermined temperature to obtain a dense ceramic body.

On the other hand, a porous ceramic body (having a large porosity) may be manufactured in the following manner, for example. Specifically, a starting material ceramic powder is first prepared in accordance with a wet or dry process. Subsequently, water, a foaming agent and the like are added to the prepared starting material ceramic powder, and then the mixed solution containing them is agitated. Next, the agitated mixture is dried at about 80° C., for example, to form a dried body having a predetermined shape. A porous ceramic body is obtained by sintering the dried body at a predetermined temperature. In this connection, examples of foaming agents include organic substance having thermal decomposition property, such as hydrogen peroxide, methylcellulose and the like.

The porosity of the porous ceramic body can be adjusted by varying the amount of the foaming agent to be added; the viscosity (that is, the ratio of powder and liquid) of the mixture containing the foaming agent and the starting material ceramic powder; the agitating conditions of the mixed solution; the sintering conditions; and the like.

The porosity of the porous ceramic body is not limited to any particular value, and it can be appropriately set in accordance with the intended application of the ceramic composite. In this connection, at least one of the ceramic bodies to be bonded should have porosity of 5 to 90%, and preferably 10 to 70%, more preferably 15 to 60%. Porosity is the ratio of total pore volume to total ceramic body volume.

When the porosity of the ceramic body is less than 5%, it is impossible for the ceramic composite to retain a drug in an adequate manner. On the other hand, when the porosity of the ceramic body is more than 90%, drug releasing rate of the sustained release carrier (that is, ceramic composite with the drug) becomes excessively high, making it impossible to extend the period of releasing the drug. In addition, when the porosity of the ceramic body exceeds 90%, the strength of the sustained release carrier is reduced, and this may result in the case that the sustained release drug carrier cannot exhibit its functional properties sufficiently. However, keeping the porosity within the aforementioned range makes it possible to obtain a ceramic composite particularly suitable for bone replacement materials.

Further, it is also preferred that the ceramic composite are formed by bonding ceramics bodies having mutually different pore diameters (pore sizes). In this case, the ceramic body with a large pore diameter has an increased drug releasing rate. On the other hand, the ceramic body with a small pore diameter has a decreased drug releasing rate. In view of the above, combining ceramic bodies having various pore diameters makes it possible to set the drug releasing rate of the entire sustained release drug carrier to a desired release rate. This means that the drug releasabilities of the sustained release drug carrier can be controlled in a simple manner.

Although the pore diameters of the ceramic bodies to be bonded are not limited in any particular value, 100 to 500 $\mu$m is preferred, and 200 to 400 $\mu$m is particularly preferred. When the pore diameter is less than 100 $\mu$m, drug impregnation is difficult to achieve, making it impossible for the ceramic composite to retain a drug in an adequate manner. On the other hand, when the pore diameter exceeds 500 $\mu$m, the drug releasing rate is excessively high, making it impossible to extend the period of releasing the drug. In addition, the strength of the ceramic composite is reduced in this case, thereby making it impossible or difficult to obtain a sustained release drug carrier having sufficient strength.

In the case where the ceramic body is prepared by agitating a mixture including ceramic powder and a water-soluble foaming agent dissolved in water, it is possible to obtain the ceramic body having such pore size by optimizing some conditions such as agitating speed and the like. Further, in the case where a foaming agent having a property that foam is disappeared by heating is used and such a foaming agent in the form of a solid state is mixed with ceramic powder to prepare the ceramic body, it is possible to obtain the ceramic body having such pore size by controlling the diameter of the particle of the foaming agent.

In this regard, it is preferred that the pores of the ceramic body include "three-dimensionally communicating pores" refers to a special pore structure composed of pores and capillaries formed by the gaps among the particles of ceramic powders, in which the pores mutually communicate with each other through the capillaries.

The fact that ceramic bodies have such three-dimensionally communicating pores means that a ceramic composite consisting of these ceramic bodies also has three-dimensionally communicating pores. These three-dimensionally communicating pores are formed with the capillaries as described above. Therefore, the drug-retention capabilities of the ceramic composite are improved by the capillary effect of these capillaries. As a result, it is possible to provide a sustained release drug carrier capable of continuously releasing a drug in a sustained manner for a long time.

In addition, body fluids (i.e., blood and the like) can flow smoothly through three-dimensionally communicating pores, making it easier for new bone cells to be formed around the sustained release drug carrier. This means that the sustained release drug carrier of the present invention has excellent affinity for bone tissue. In this connection, it should be noted that the sustained release drug carrier of the present invention, in addition to having such properties, has a sufficient strength required for a bone replacement material.

Capillaries of at least one of the ceramic bodies should have a diameter of approximately 0.1 to 20 $\mu$m, and preferably approximately 0.5 to 10 $\mu$m. By controlling the ceramic powder particle size, the capillary diameters can be controlled. When the diameter of capillaries is less than 0.1 $\mu$m, it is impossible to increase an amount of drug to be retained by the ceramic composite. Further, there is a case that it would be impossible for the sustained release drug carrier to release the drug in a smooth manner. On the other hand, when the diameter of capillaries is greater than 20 $\mu$m, it is impossible to achieve an extended period of releasing the drug, and there is a risk that the strength of the sustained release drug carrier is decreased.

Further, spherical ceramic powders prepared using a drier such as a spray drier and the like should preferably be used to obtain a ceramic body having such capillaries.

Ceramic bodies to be bonded may have different compositions, but it is preferred that they have the identical compositions. In this connection, it is to be noted that bonding flaws may occur during sintering process if ceramic bodies to be bonded have different compositions and they possess significantly different coefficients of thermal shrinkage.

No limitations are imposed on the materials that constitute the ceramic bodies. Preferably, ceramic materials that have bioaffinity and biosafety should be used as constituent materials for the ceramic bodies. In other words, various ceramic materials having biocompatibility can be used.

Examples of ceramic materials that can be used as such biocompatible materials include alumina, zirconia, calcium phosphate-based compounds, and the like. In this connection, calcium phosphate-based compounds should preferably be used as the biocompatible materials, since calcium phosphate-based compounds can remain stable in the living body for a long time and therefore they are particularly suitable for biocompatible materials.

Examples of calcium phosphate-based compounds include hydroxyapatite ($Ca_{10}(PO_4)_6(OH)_2$), TCP ($Ca_3(PO_4)_2$), $Ca_2P_2O_7$, $Ca(PO_3)_2$, $Ca_{10}(PO_4)_6F_2$, $Ca_{10}(PO_4)_6Cl_2$, DCPD ($CaHPO_4 \cdot 2H_2O$), and $Ca_4O(PO_4)_2$. These may be used individually or as mixtures of two or more compounds.

The Ca/P ratio of such a calcium phosphate-based compound should preferably be 1.0 to 2.0. A calcium phosphate-based compound whose Ca/P ratio lies within this range has excellent biostability and biocompatibility, and is thus suitable for a biocompatible material. When a ceramic body is formed of a mixture containing various kinds of calcium phosphate-based compounds, the Ca/P ratio of the mixture should preferably lie within the above-mentioned range.

Among the calcium phosphate-based compounds, hydroxyapatite is extremely suitable for biocompatible materials such as artificial bone, artificial dental implants and the like, since hydroxyapatite has a structure that is similar to bone or dental tissue. Therefore, hydroxyapatite should preferably be used as constituent materials for the ceramic composite (which is used for constituting the sustained release drug carrier of the present invention).

The ceramic composite obtained in this manner should preferably be used as a bone replacement material such as vertebral spacer. In this connection, when biocompatible materials such as hydroxyapatite are used as constituent materials for the ceramic composite, it becomes possible to obtain the ceramic composite having tissue affinity in addition to the drug retention capabilities.

Substances to be carried by the sustained release drug carrier of the present invention is not limited to drugs.

Examples of substances that can be carried by the sustained release drug carrier of the present invention include aromatics; preservatives; and the like in addition to biologically active substances such as medical preparations, insecticides, antifungal agents, repellents, bactericides, nutrients, and the like. Among these substances, biologically active substances including drugs are particularly preferred as substances to be carried by the sustained release drug carrier of the present invention.

When the sustained release drug carrier of the present invention is used in order to administer biologically active substances such as medical preparations, it is possible to maintain much more stable level of the concentration of the drug in blood and to maintain this state for a longer time in comparison with the case where the drug is administered through oral or parenteral administration. As a result, it becomes possible to avoid serious side effects from being caused by the drug.

Examples of medical preparations that can be used in the sustained release drug carrier of the present invention include bone morphogenic protein (BMP), antibiotics, anti-inflammatory agents, antitumor agents, and the like.

Hereinafter, a description of a method for manufacturing the ceramic composite used for the sustained release drug carrier of the present invention will be given.

Figure 1:
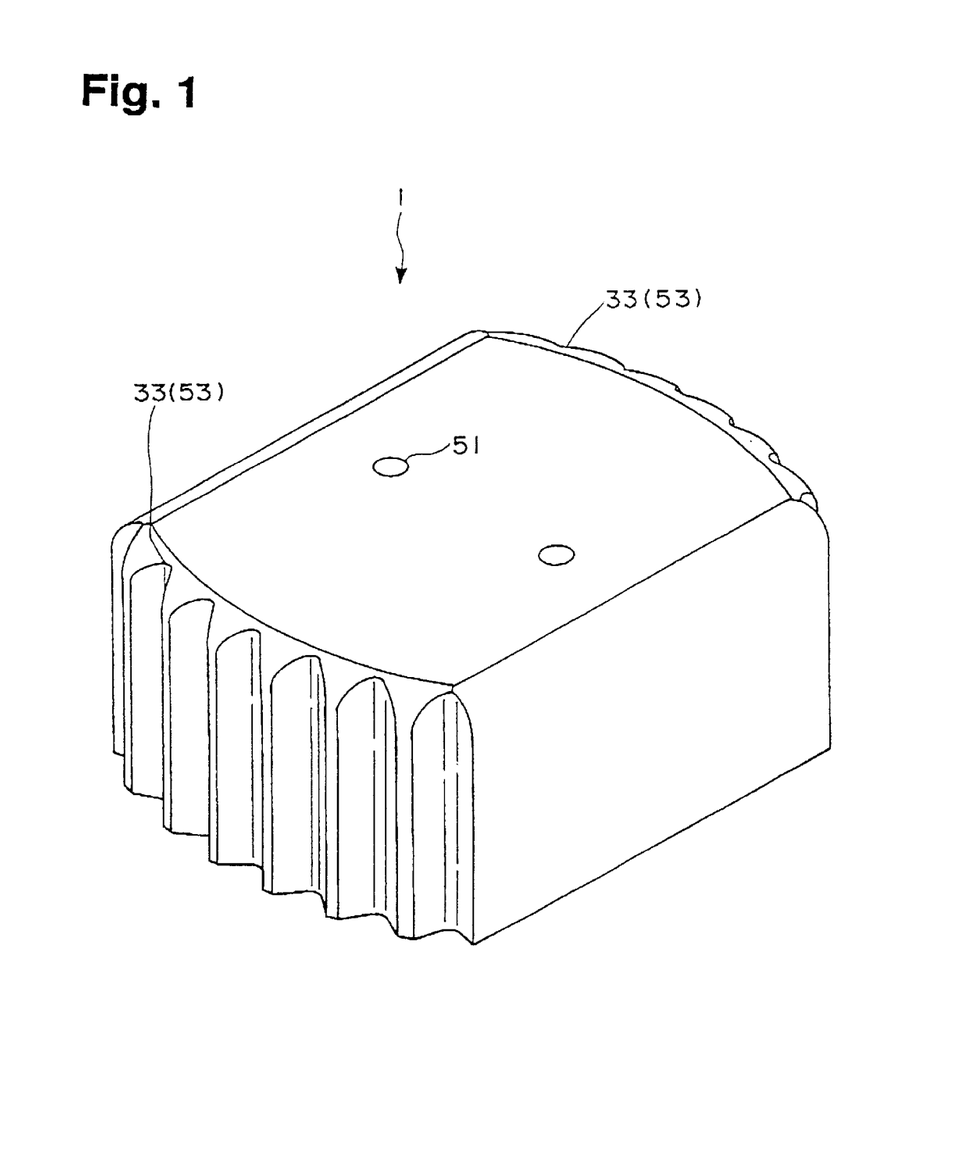
FIG. 1 is a perspective view which shows a first embodiment of a sustained release drug carrier (vertebral spacer with drugs) according to the present invention.
Figure 2:
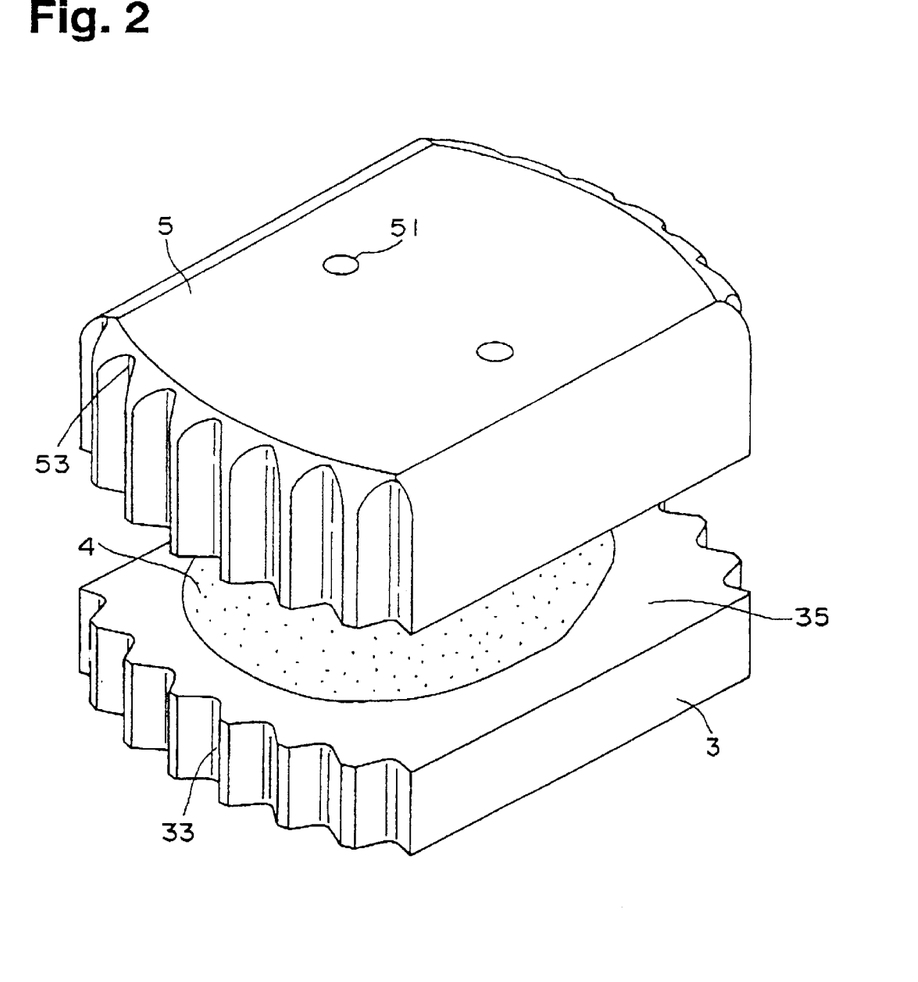
FIG. 2 is a perspective view of ceramic bodies to be bonded in accordance with a method of the present invention, which shows a state that a slurry is applied to a bonding surface of one of the ceramic bodies.
Figure 3:
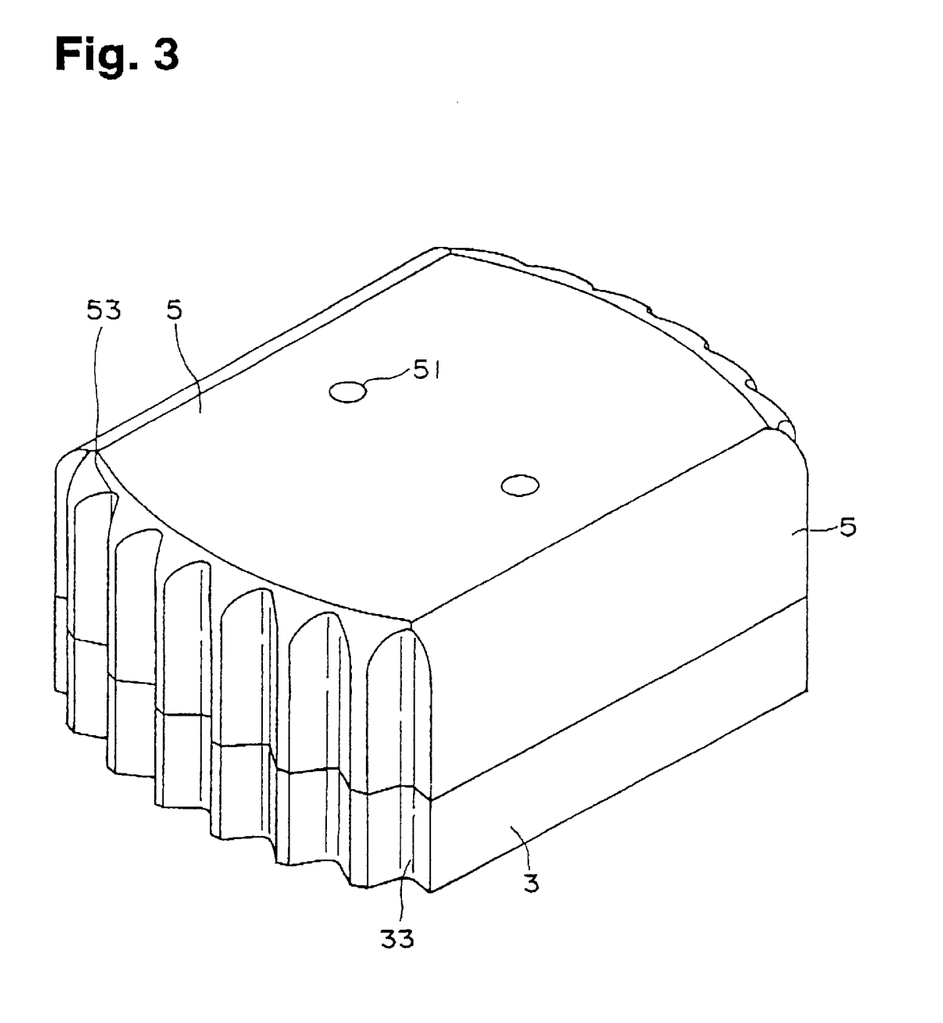
FIG. 3 is a perspective view which shows a state that the ceramic bodies in FIG. 2 are superposed.

FIG. 1 is a perspective view which shows a sustained release drug carrier (vertebral spacer with drug) according to the present invention. FIG. 2 is a perspective view of ceramic bodies to be bonded in accordance with the method of the present invention, which shows a state that a slurry is applied to a bonding surface of one of ceramic bodies. FIG. 3 is a perspective view which shows a state that the ceramic bodies in FIG. 2 are superposed.

As can be seen from the drawings, a method for manufacturing the ceramic composite used for the sustained release drug carrier 1 of the present invention comprises the following steps.

(i) First, ceramic bodies to be bonded together are prepared. Further, a slurry in which primary particles of a bonding ceramics are dispersed is prepared.
(ii) The slurry is applied to the bonding surface of at least one of the ceramic bodies to be bonded.
(iii) Then, the ceramic bodies between which the slurry has been interposed is sintered to bond them together to obtain a ceramic composite.

The details of the method for manufacturing the ceramic composite used for the sustained release drug carrier 1 is as follows.

A slurry 4 containing primary particles of a bonding ceramics in a dispersed form is interposed on the bonding surface 35 between ceramic bodies 3 and 5, as shown in FIG. 2. The ceramic bodies are firmly bonded together by sintering the composite in the state shown in FIG. 3, thereby making it possible to obtain an integrated ceramic composite.

In this case, when at least one of the ceramic bodies to be bonded is a porous ceramic body, the bonding ceramics in the slurry enters into the pores of the porous ceramic body. Thus, it becomes possible to increase the contacting surface area between one ceramic body and the other ceramic body, because pores located at the bonding surface of the ceramic body are filled with the bonding ceramics. Further, it also becomes possible to bond the ceramic bodies such that an anchoring effect is obtained. As a result, the bonding strength between the ceramic bodies is further enhanced.

When sintering the ceramic bodies between which the slurry has been interposed, the particles (primary particles) of the bonding ceramics in the slurry react with adjacent particles and then grow into larger particles. Repeating such particle growth allows the ceramic bodies to be bonded to each other. In addition, since the sintered bonding ceramics has the same strength as that of the ceramic bodies, a ceramic composite having uniform strength can be obtained. Such a ceramic composite is capable of preventing the strength at the bonding area between the ceramic bodies from being lowered.

The disperse medium to be contained in the slurry should preferably be inorganic disperse medium such as water. Therefore, the slurry does not contain any water-soluble polymers such as binders which are commonly used as bonding materials. Thus, ceramic composites having no organic components can be obtained. Accordingly, the ceramic composite for the sustained release drug carrier of the present invention does not contain any organic components, thus eliminating the danger that these organic components will elute into the living body when it is used in the living body. This means that the sustained release drug carrier of the present invention has excellent biosafety.

In addition, since the slurry does not contain any high-viscosity substances such as water-soluble polymers as described above, the bonding ceramics can be dispersed in the slurry uniformly and easily. This means that the slurry used during the manufacture of the sustained release drug carrier of the present invention has excellent workability and handling ability.

When a calcium phosphate-based ceramic is used as the bonding ceramic, the slurry 4 in which primary particles of the bonding ceramics are dispersed may be obtained, for example, by a known wet method in which a phosphoric acid aqueous solution in the form of droplet is added to a calcium hydroxide slurry.

The bonding ceramics should preferably be constituted from the same ceramic material as that of at least one of the ceramic bodies to be bonded.

When the bonding ceramics in the slurry which is constituted from the same material as that of the ceramic body is used to bond the ceramic bodies together, no boundary surface is formed between the slurry and the one ceramic body, thereby enabling to enhance or improve the bonding strength of the ceramic bodies.

In this connection, it is of course possible to form both the ceramic bodies from the same material as that of the bonding ceramics in the slurry.

In this case, for the same reasons as those described above with reference to the ceramic bodies, it is preferable that the ceramic material used for the bonding ceramics is composed of a calcium phosphate-based compound, preferably one with a Ca/P ratio of 1.0 to 2.0, and more preferably hydroxyapatite.

Although the content of the bonding ceramics in the slurry is not limited to any particular value, a content of about 0.1 to 20 vol % is preferred. When the content of the bonding ceramics is less than 0.1 vol %, there is a case that the bonding ceramics fails to exhibit an adequate effect, thereby resulting in inferior bonding strength. On the other hand, when the content of the bonding ceramics exceeds 20 vol %, the fluidity of the slurry becomes lowered, which may result in poor handling ability and workability.

It is preferable that the particles (primary particles) of the bonding ceramics have an average grain size of 0.05 to 0.5 $\mu$m, and more preferably 0.1 to 0.3 $\mu$m. When the average grain size of the bonding ceramics is less than 0.05 $\mu$m, there is a case that an adequate bonding effect will not be obtained. On the other hand, when the average grain size exceeds 0.5

μm, it is not always possible to keep the density of the bonding ceramics in the slurry uniformly. Consequently, there is a case that nonuniform sintering and dispersion in the bonding strength will occur.

No limitations are imposed on the method for applying the above-mentioned slurry to the bonding surface. Examples of the applying methods include the following methods.

(i) A method in which the slurry is merely applied to the bonding surface.

(ii) A method in which the slurry is impregnated into the bonding surface.

(iii) A method in which the slurry is sprayed against the bonding surface.

(iv) A method in which the slurry is dropped onto the bonding surface.

Further, it is also possible to use a method in which the bonding surfaces of the ceramic bodies are immersed in the slurry. Furthermore, the slurry may also be applied to the bonding surface by any combination of these methods.

After the slurry has been applied between the ceramic bodies, the two ceramic bodies may be compressed to evenly spread the slurry across the bonding surfaces thereof, if necessary.

Examples of sintering methods which can be used in the method for manufacturing a ceramic composite used for a sustained release drug carrier of the present invention include pressureless sintering, hot plasma sintering, microwave sintering and the like; and pressure sintering method such as hot pressing (HP), spark plasma sintering (SPS), hot isostatic pressing (HIP) and the like. Among these methods, the pressureless sintering method is preferably utilized to manufacture the ceramic composite.

The above-described pressure sintering method is advantageous in that it is possible to manufacture ceramic composites having complex shapes. This means this method is capable of providing wide versatility on shape.

On the other hand, the non-pressure sintering method is advantageous in that simpler sintering equipment and sintering process can be used as compared with the pressure sintering method, thereby making it possible to improve manufacturing efficiency.

The sintering temperature is appropriately set depending on the sintering methods or the materials constituting the ceramic bodies. Preferably, this temperature is set to a temperature of 900 to 1300° C., and more preferably 1000 to 1200° C. When the sintering temperature is lower than 900° C., it is sometimes impossible to obtain adequate bonding strength due to incomplete sintering. On the other hand, when the temperature exceeds 1300° C., there is a case that heat will induce decomposition in the bonding ceramics and the ceramic materials constituting the ceramic bodies, which may result in a case where an excellent ceramic composite cannot be obtained.

Hereinbefore, a method for producing ceramic composites was described. In this connection, it should be noted that in this invention a ceramic composite may be produced by interposing the slurry between sintered ceramic bodies, and then sintering the ceramic bodies with the slurry to bond them together. Further, a ceramic composite may also be produced by interposing the slurry between unsintered ceramic bodies, and then sintering the ceramic bodies with the slurry to bond them together.

Next, in order to obtain a sustained release drug carrier, a drug is impregnated into the ceramic composite prepared in the manner described above.

Examples of methods for impregnating a liquid drug into a ceramic composite include the following methods.

(i) A method in which the ceramic composite is immersed in a liquid drug.

(ii) A method in which a drug is diluted with a diluent, and then the ceramic composite is immersed in the diluted drug solution.

(iii) A method in which the ceramic composite is immersed in a drug solution, and then the drug is impregnated under a reduced pressure.

(iv) A method in which the ceramic composite is immersed in a drug solution, and then the drug is impregnated using a centrifugal separator or the like.

Among the above methods, the methods (iii) and (iv) allow the drug to be impregnated deeply and securely into the ceramic composite. Further, using these methods also allows maximum possible amount of a drug to be retained by the ceramic composite.

When a solid drug has to be retained by a ceramic composite, it is necessary to first dissolve or suspend the drug in an appropriate solvent, yielding a liquid-type drug. The liquid-type drug is then impregnated into the ceramic composite by the same method as that used to impregnate a liquid drug.

Then, the ceramic composite retaining the liquid-type drug may be dried, if necessary. In this case, drying method such as heat drying, freeze drying and the like may be used to dry the ceramic composite with the liquid-type drug. In this connection, heat drying should preferably be performed by heating the ceramic composite in a high-temperature drier (at about 100° C. or lower). Further, when the drug is apt to deteriorate or decompose under heating, the ceramic composite should preferably be dried by freeze drying.

The sustained release drug carrier of the present invention and the method for manufacturing the sustained release drug carrier were described above with reference to the embodiments shown in the appended drawings. In this connection, it is to be noted that the present invention is not limited to the above-described embodiments. For example, the sustained release drug carrier of the present invention may have any shape, and may be manufactured in accordance with any methods.

EXAMPLES

Hereinafter, specific examples of the present invention will be described.

1. Manufacture of Sustained Release Drug Carrier
(Example 1)

According to a known wet method, a phosphoric acid aqueous solution in the form of droplet was added to a calcium hydroxide slurry to obtain a hydroxyapatite slurry containing 10 vol % of primary particles of a hydroxyapatite having a Ca/P ratio of 1.67 and an average grain size of 0.1 μm.

Further, the hydroxyapatite slurry obtained in accordance with the above-described wet method was sprayed and then dried to obtain the spherical powder (secondary particles) of hydroxyapatite. Then, after pre-sintering the obtained spherical powder at 700° C., it was ground (milled) so that a small amount of fine powder of hydroxyapatite remains in the obtained spherical powder in which most of the particles maintain their spherical shape. (Note: By containing such fine powder, the particles are sintered under the condition that the fine powder is stuck to contacting portions between the particles, thereby contributing to improve bonding strength between the particles in a sintered compact.)

Subsequently, the ground hydroxyapatite powder was added in a predetermined ratio to an aqueous solution of natural macromolecular compound such as methylcellulose and the like. Then, the mixed solution was agitated until the solution was foamed. The foamed solution was subsequently dried at about 80° C. to obtain unsintered ceramic bodies 3, 3', 5 and 5' as shown in FIGS. 2 and 8.

Figure 8:
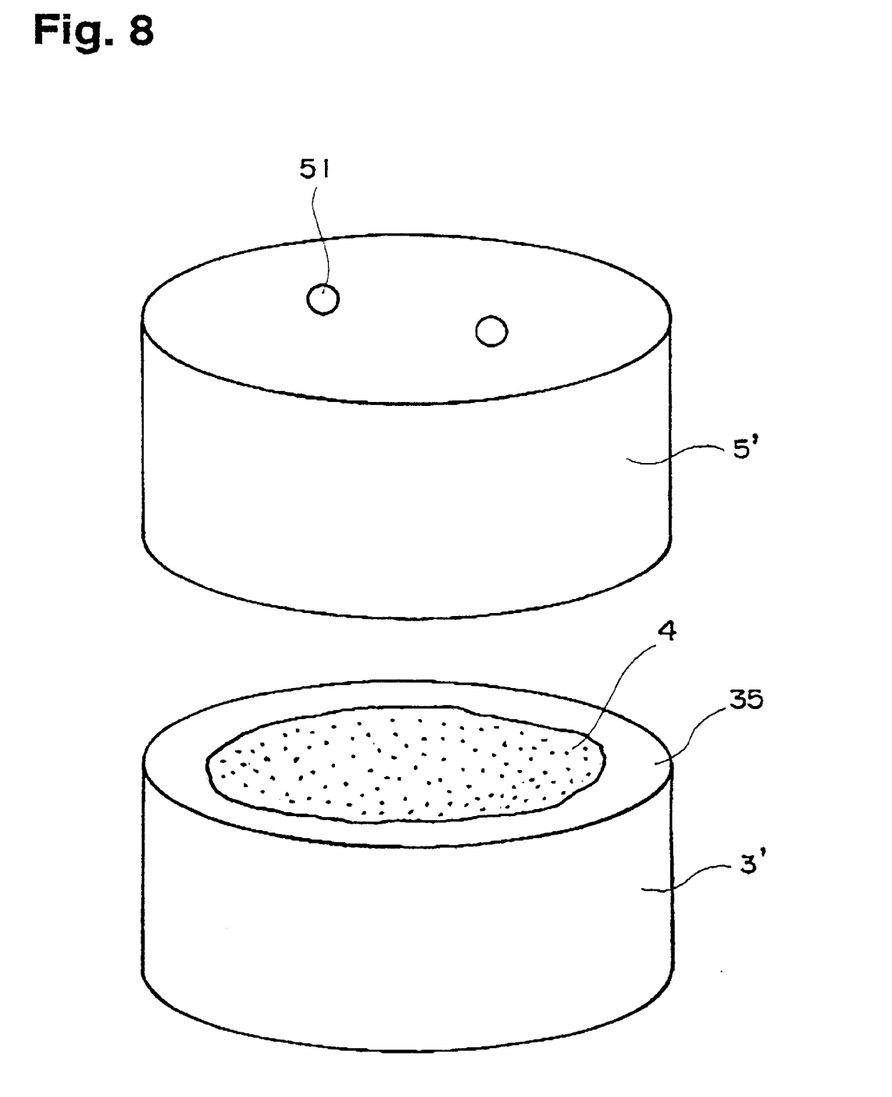
FIG. 8 is a perspective view of ceramic bodies to be bonded in accordance with a method of the present invention, which shows a state that a slurry is applied to a bonding surface of one of the ceramic bodies.

As shown in FIGS. 2 and 8, two openings 51 were formed near the center of the top surface of the ceramic body. The presence of these openings were used to indicate that the ceramic body 5 (5') had a higher porosity than the ceramic body 3 (3').

Subsequently, an appropriate amount of slurry 4, which had been prepared in advance, was applied to the bonding surface 35 of the ceramic body 3 as shown in FIG. 2, and then the ceramic body 5 was superposed thereon (see FIG. 3). Further, in the case of the embodiment shown in FIG. 8, a slurry 4 was applied to the bonding surface 35 of the ceramic body 3' in the same manner as the embodiment shown in FIG. 2, and then the ceramic body 5' was superposed thereon (see FIG. 9).

Then, the ceramic bodies 3 and 5 in the state shown in FIG. 3 were sintered for 2 hours at a sintering temperature of 1200° C. by a normal-pressure sintering method to obtain a ceramic composite. In this way, ceramic composites for a vertebral spacer used for a sustained release drug carrier having different porosities were manufactured (Examples 4–6). Each of the ceramic composites obtained in Examples 4–6 had a generally rectangular parallelepiped shape as shown in FIG. 1 (width: 15 mm, maximum length: 20 mm, height: 7 mm). Further, as shown in FIG. 1, each ceramic composite had engagement grooves 33 (53) on its opposite lateral surfaces. These engagement grooves 33 (53) were formed to allow the vertebral spacer to be securely fixed in place in an implantation area. In other words, the engagement grooves 33 (53) prevent the vertebral spacer from being dislodged from the implantation area.

Figure 7:
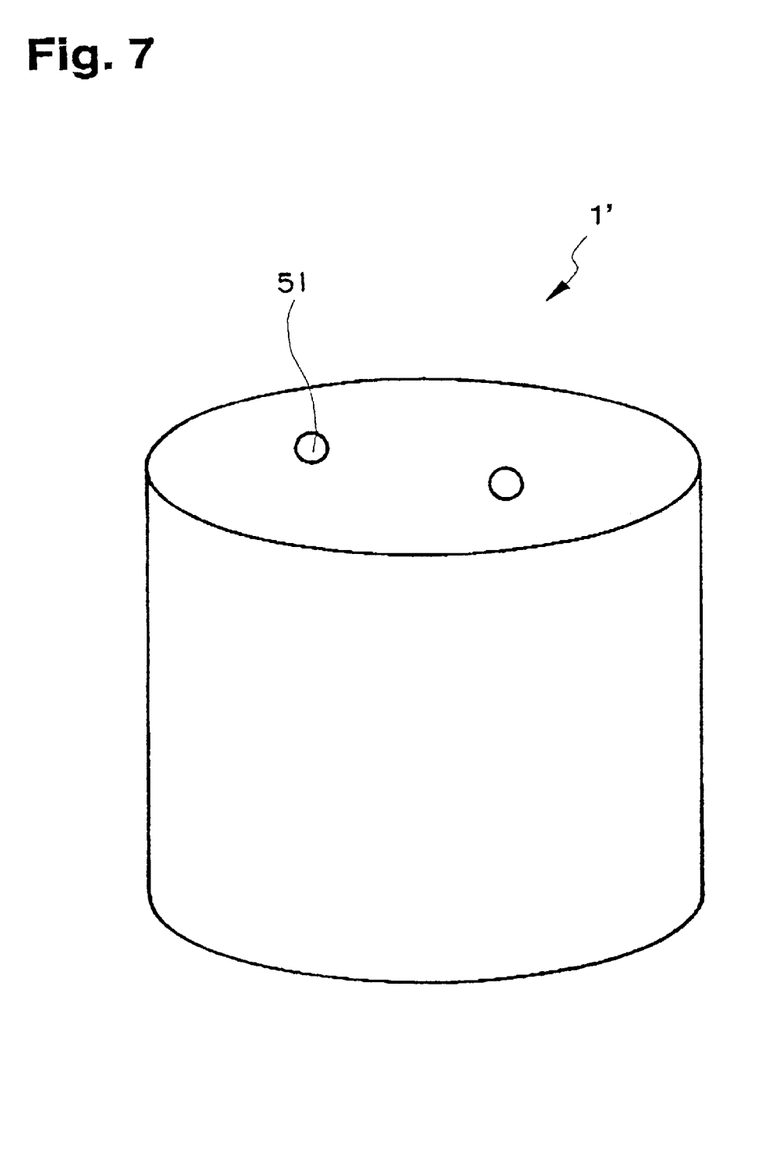
FIG. 7 is a perspective view which shows a second embodiment of the sustained release drug carrier according to the present invention.
Figure 9:
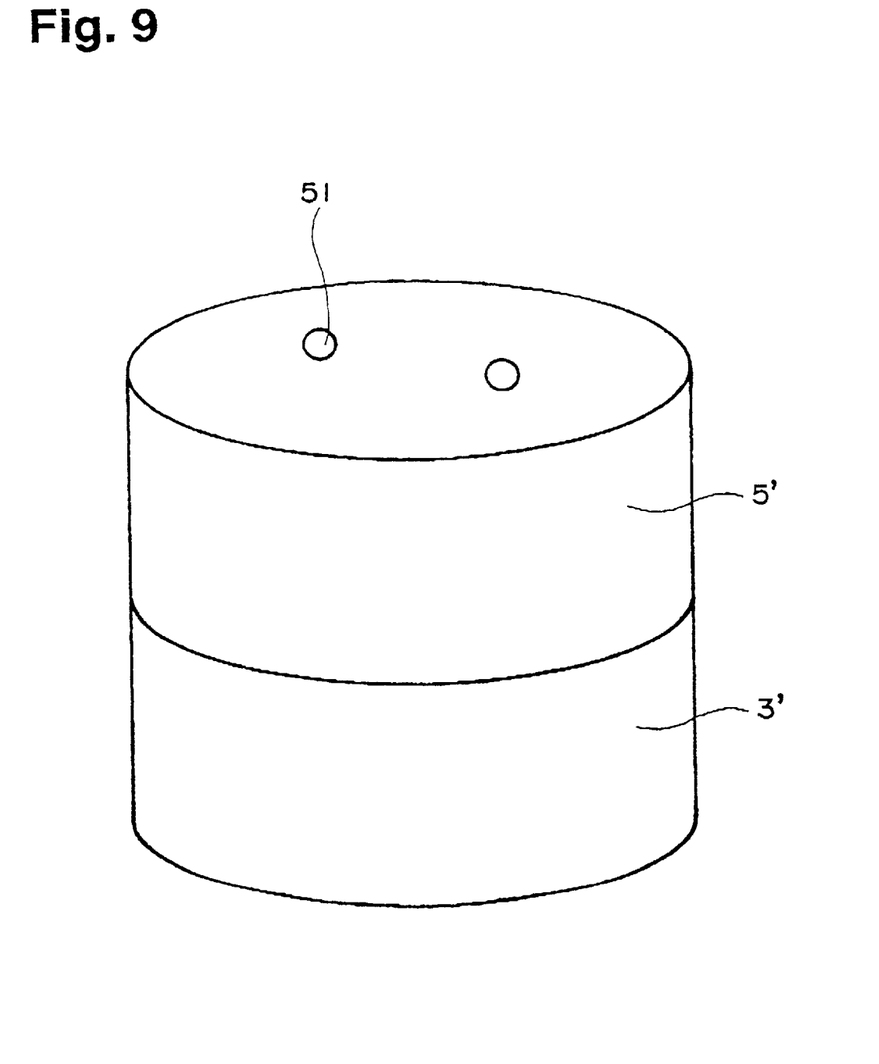
FIG. 9 is a perspective view which shows a state that the ceramic bodies in FIG. 8 are superposed.

Further, the ceramic bodies 3' and 5' in the state shown in FIG. 9 were sintered for 2 hours at a sintering temperature of 1200° C. by a normal-pressure sintering method to obtain a ceramic composite. In this way, ceramic composites used for a sustained release drug carrier having different porosities were manufactured (Examples 1–3). Each of the ceramic composites obtained in Examples 1–3 had roughly cylindrical shape as shown in FIG. 7 (diameter: 5 mm, height: 4 mm).

The details of each of the ceramic composites obtained in Examples 1–6 are summarized in Table 1.

TABLE 1

|  |  | EX. 1 | EX. 2 | EX. 3 | EX. 4 | EX. 5 | EX. 6 |
|---|---|---|---|---|---|---|---|
| Section Originating in Ceramic Body 3 (3') | Pore Diameter ($\mu$m) | 300 | 300 | 300 | 300 | 300 | 300 |
|  | Capillary Diameter | 2–3 | 2–3 | 2–3 | 2–3 | 2–3 | 2–3 |
|  | Porosity (%) | 30 | 40 | 50 | 30 | 40 | 50 |
| Section Originating in Ceramic Body 5 (5') | Pore Diameter ($\mu$m) | 300 | 300 | 300 | 300 | 300 | 300 |
|  | Capillary Diameter ($\mu$m) | 2–3 | 2–3 | 2–3 | 2–3 | 2–3 | 2–3 |
|  | Porosity (%) | 50 | 50 | 50 | 50 | 50 | 50 |

Next, for each of the ceramic composites obtained in Examples 1–6, the area near the bonding surface was observed visually and by electron microscope, respectively. Through this observation, it was found that the ceramic body 3 (3') and the ceramic body 5 (5') had been completely integrated such that the bonding surface could not be seen even with the electron microscope.

Further, it was also confirmed that three-dimensionally communicating pores were formed in each of the ceramic composites obtained in Examples 1–6.

Next, indomethacin was impregnated into each of the ceramic composites obtained in Examples 1–6. Specifically, an indomethacin solution was first introduced into a drier whose pressure can be reduced. Then, each of the ceramic composites were respectively immersed in the indomethacin solution. The pressure in the drier was subsequently set to 10 mmHg and kept at this level for 60 minutes. Vacuum drying was then performed for 5 hours at 30° C. Thus, the sustained release drug carrier 1 (that is, the vertebral spacer with the indomethacin) as shown in FIG. 1 and the sustained release drug carrier 1' with the indomethacin as shown in FIG. 7 were obtained.

2. Test for Sustained Drug Releasability

For each of the sustained release drug carriers 1' obtained in Examples 1 to 3, the sustained drug releasability of indomethacin was tested. The test was performed according to the following procedure. Specifically, first, each of the sustained release drug carriers 1' was immersed in 500 mL of a 0.1 M phosphate buffer solution (pH=7.4) kept at a temperature of 37° C. Then, a magnetic stirrer was rotated at 200 rpm to stir the solution. The solution was periodically sampled, and quantitative analysis was made for the amount of eluated (released) indomethacin. This analysis was carried out in accordance with the absorptiometric method (254 nm).

Figure 4:
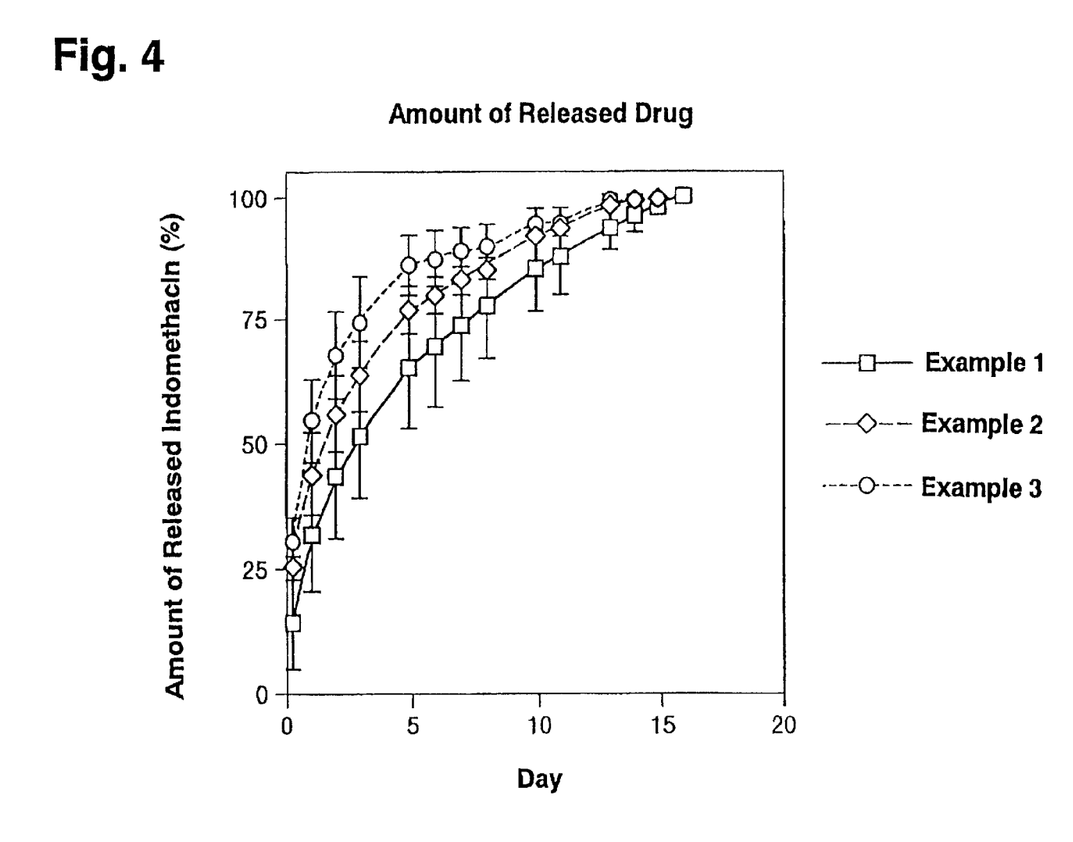
FIG. 4 is a graph which shows the results of the test for sustained drug releasabilities of the examples of the sustained release drug carrier (vertebral spacer with drugs) according to the present invention.

The test results are shown in FIG. 4.

It can be seen in FIG. 4 that the sustained drug releasability of the sustained release drug carrier of the present invention can be adjusted. Namely, FIG. 4 shows the fact that each of the sustained release drug carriers of Examples 1 to 3 released the different amount of the drug within the same period, that is the drug releasability of the respective sustained release drug carriers was adjusted.

Consequently, according to the sustained release drug carrier of the present invention, it is possible to release a drug in a sustained manner at a rate optimal for the application site. Further, according to the sustained release drug carrier of the present invention, it is also possible to release a drug in a sustained manner at a rate optimal for the type of drug to be administered.

Further, for example, by increasing the proportion of low-porosity areas in the sustained release drug carrier, it becomes possible to obtain a sustained release drug carrier capable of releasing drugs in a sustained manner for a long time. This means that the drug release period of the sustained release drug carrier can be easily controlled by varying the size of the ceramic bodies to be bonded together, the porosity of the respective ceramic bodies, and the like.

The same experiments were performed on the vertebral spacers of Examples 4 to 6, and substantially the same results as those in Examples 1 to 3 were obtained.

3. Application of Sustained Release Drug Carrier into Living Body

Hereinafter, an evaluation for the case where the sustained release drug carrier (vertebral spacer with drug) was applied into a living body will be described with reference to FIGS. 5 and 6.

Figure 5:
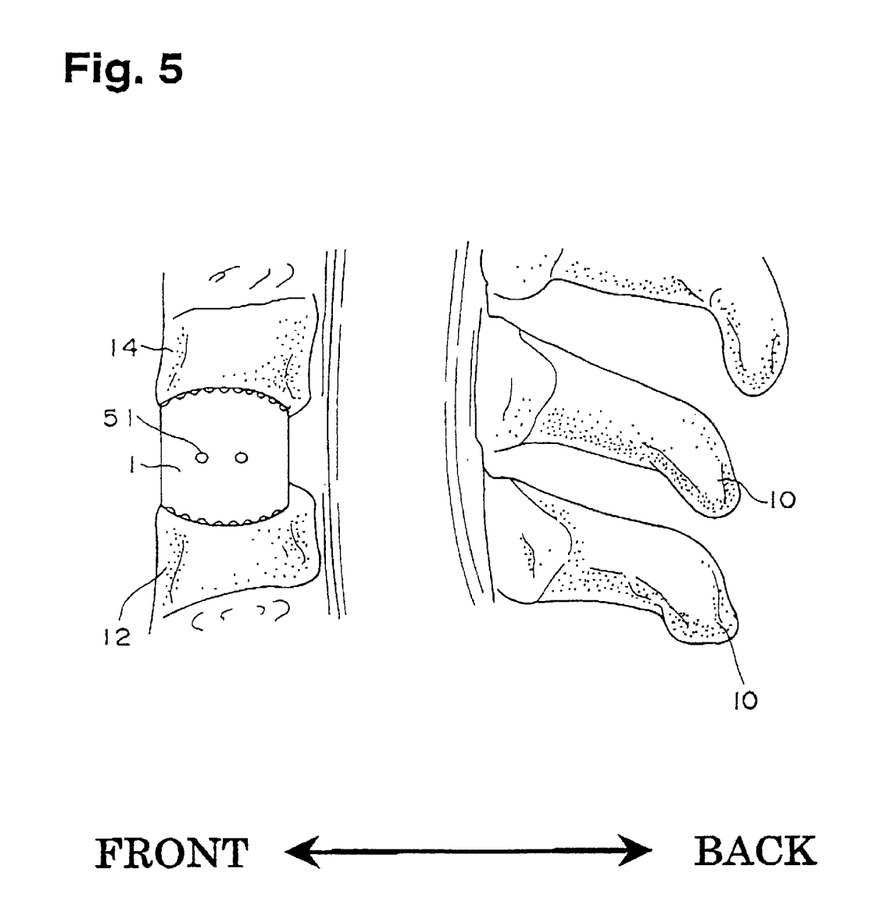
FIG. 5 is a front view which shows a state in which the sustained release drug carriers (vertebral spacers with drugs) of the present invention are implanted into and fixed to a cervical vertebrae.
Figure 6:
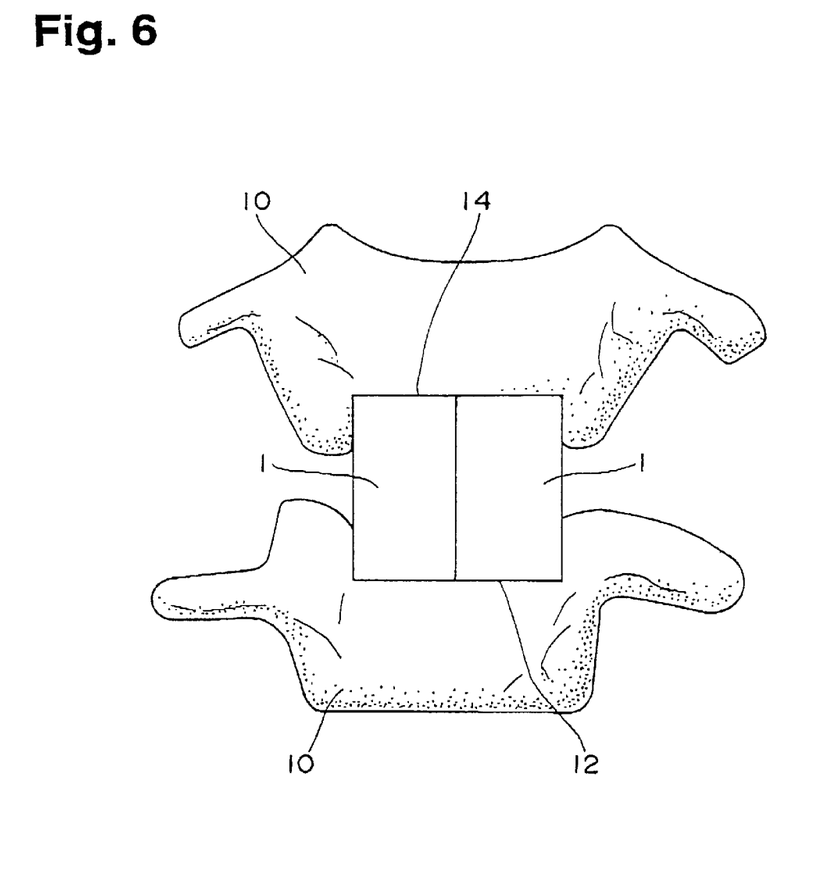
FIG. 6 is a side view which shows a state in which the sustained release drug carriers is implanted into and fixed to a cervical vertebrae.

FIG. 5 is a front view which shows a state in which the sustained release drug carriers 1 are implanted into and fixed to cervical vertebrae 10, and FIG. 6 is a side view thereof.

First, the sustained release drug carriers 1 manufactured in Examples 4–6 were prepared, in which two carriers were prepared for each of the Examples.

Next, the operation of decompressing and fusing anterior cervical vertebrae was performed on the patient who needs the decompression and fusion of his anterior cervical vertebrae across the space between vertebral bodies, by cutting and eliminating the region of the vertebral bodies corresponding to the compressed area of the spinal cord, thereby decompressing for the cervical vertebrae 10 was performed.

After the cervical vertebrae 10 had been decompressed, two superposed sustained release drug carriers 1 (prepared in advance) were inserted (implanted) into the space between the vertebral bodies 12 and 14 of the cervical vertebrae 10, as shown in FIGS. 5 and 6. During the insertion of the sustained release drug carriers 1 into the cervical vertebrae 10, an engagement was made between the engagement grooves and the vertebral bodies 12 and 14 to fix firmly the two superposed sustained release drug carriers 1 in the space.

With respect to the state shown in FIG. 5, it should be noted that the two sustained release drug carriers 1 were superposed and inserted such that the low-porosity portions are positioned on the inside thereof (that is, the low-porosity portions face to each other), and the high-porosity portions are positioned on the outside.

In this way, the constricted portions of the cervical vertebrae was satisfactory expanded, and then this expanded state was maintained.

Further, X-ray imaging observation was carried out immediately after the surgery, and the obtained image showed transparent layers indicating the presence of spaces in the interface portions between the sustained release drug carriers 1 and the vertebral bodies 12 and 14. However, these transparent layers have disappeared in a relatively short time after the surgery as a result of bone cohesion.

Furthermore, since the strength of the sustained release drug carriers 1 on the whole was ensured by the low-porosity portions positioned inside thereof, it was possible to keep the distance between the vertebral bodies 12 and 14 in a desired interval.

As described above, the method of manufacturing the sustained release drug carrier according to the present invention makes it possible to bond a plurality of ceramic bodies with a simple technique.

In addition, according to the present invention, a slurry in which primary particles of a bonding ceramics are dispersed is applied to the bonding surface of one of the ceramic bodies to be bonded. Therefore, by sintering such ceramic bodies, it becomes possible to obtain the ceramic composite (which is used for constituting the sustained release drug carrier) having an excellent bonding strength. Further, the ceramic bodies are completely integrated with each other, thereby preventing the strength at the bonding area between the sintered ceramic bodies from being deteriorated.

Further, according to the present invention, since there is no limitation on shapes and compositions of the ceramic bodies to be bonded, it is possible to easily manufacture ceramic composites (for sustained release drug carriers) having complex shapes and composed of ceramic bodies having different porosities. Bonding such ceramic bodies having different porosities together makes it possible to obtain a sustained release drug carrier in which different sections exhibit different functions such as drug releasability. Further, it is also possible to manufacture, with a simple technique, a sustained release drug carrier having portions each having required properties such as strength, excellent bioaffinity and biosafety and the like. For example, the ceramic bodies may have different strengths including a first ceramic body having a higher strength than the strength of a second ceramic body.

In particular, when the ceramic composites for the sustained release drug carrier of the present invention is configured as a bone replacement material, and biologically active substances such as bone morphogenic protein, antibiotics and the like are impregnated into the ceramic composites, it becomes possible to provide a rigid bone replacement material having additional functions such as tissue affinity, sustained drug releasability and the like.

Finally, it is to be understood that many changes and additions may be made to the embodiments described above without departing from the scope and spirit of the invention as defined in the appended claims.

Further, it is also to be understood that the present disclosure relates to subject matter contained in Japanese Patent Application No. 11-254470 (filed on Sep. 8, 1999) which is expressly incorporated herein by reference in its entirely.

What is claimed is:

1. A sustained release carrier, comprising:
   a ceramic composite which is formed by bonding at least a first porous ceramic body having its own overall porosity in the range of 15 to 60%, and a second porous ceramic body having its own overall porosity in the range of 15 to 60%; the first and second porous ceramic bodies comprising a calcium phosphate-based ceramic compound; the first and second porous ceramic bodies each having a bonding surface; the first and second porous ceramic bodies being bonded together with a bonding ceramic applied as a slurry to the bonding surfaces of the first and second ceramic bodies; wherein the slurry comprises primary particles of the same ceramic compound of which the first and second said bodies are comprised; and
   active substance(s) impregnated into the first and second porous ceramic bodies;
   wherein the overall porosity of the first porous ceramic body is different from the porosity of the second porous ceramic body thereby providing different release rates of the active substance(s).

2. The carrier of claim 1, wherein the first ceramic body has a lower porosity than the second ceramic body and the first ceramic body exhibits a release rate of the active substance(s) that is lower than the release rate of the second ceramic body as a result of the lower porosity of the first ceramic body.

3. The carrier of claim 1, wherein the first ceramic body has a higher strength than the strength of the second ceramic body.

4. The carrier of claim 1, wherein the average pore size of at least one of the ceramic bodies is 100 to 500 $\mu$m.

5. The carrier of claim 1, wherein the average pore size of at least one of the ceramic bodies is 200 to 400 $\mu$m.

6. The carrier of claim 1, wherein the pores of at least one of the ceramic bodies include three-dimensionally communicating pores comprising capillaries.

7. The carrier of claim 6, wherein the average pore size of the capillaries is 0.1 to 20 $\mu$m.

8. The carrier of claim 6, wherein the average pore size of the capillaries is 0.5 to 10 $\mu$m.

9. The carrier of claim 1, wherein at least one of the ceramic bodies comprises a Ca/P ratio of 1 to 2.

10. The carrier of claim 1, wherein the active substance(s) comprises a biologically active agent(s).

11. The carrier of claim 10, wherein the biologically active agent(s) comprises a drug(s).

12. The carrier of claim 9, wherein at least one of the ceramic bodies comprises hydroxyapatite.

13. A bone replacement material comprising the carrier of claim 1.

14. A vertebral spacer comprising the carrier of claim 1.

15. A bone implant comprising the carrier of claim 1.

16. A sustained release carrier for releasing an active substance(s) impregnated therein, comprising:

a ceramic composite into which the active substance(s) can be impregnated, the ceramic composite formed by bonding at least a first porous ceramic body having its own overall porosity in the range of 15 to 60%, and a second porous ceramic body having its own overall porosity in the range of 15 to 60%; the first and second porous ceramic bodies comprising a calcium phosphate-based ceramic compound; the first and second porous ceramic bodies each having a bonding surface; the first and second porous ceramic bodies being bonded together with a bonding ceramic applied as a slurry to the bonding surfaces of the first and second ceramic bodies; wherein the slurry comprises primary particles of the same ceramic compound of which the first and second said bodies are comprised; wherein the overall porosity of the first porous ceramic body is different from the porosity of the second porous ceramic body thereby providing different release rates of the active substance(s).

17. A method of manufacturing a sustained release carrier comprising:

preparing first and second porous ceramic bodies from powder(s) comprising a calcium phosphate-based ceramic compound;

the first porous ceramic body having its own overall porosity in the range of 15 to 60%, and the second porous ceramic body having its own overall porosity in the range of 15 to 60%;

wherein the overall porosity of the first porous ceramic body is different from the overall porosity of the second porous ceramic body;

the first and second porous ceramic bodies each having a bonding surface;

preparing a slurry of bonding ceramics in which primary particles of the same ceramic compound of which the first and second said bodies are comprised are dispersed;

interposing the slurry between the first and second bodies;

sintering the first and second bodies to obtain a ceramic composite; and impregnating an active substance(s) into the ceramic composite.

18. The method of claim 17, wherein the bonding ceramics comprise a calcium phosphate-based compound.

* * * * *